United States Patent
Yamada et al.

[11] Patent Number: 5,126,459
[45] Date of Patent: Jun. 30, 1992

[54] PROCESS FOR PREPARING 5-ARYLHYDANTOIN

[75] Inventors: Masahiko Yamada; Satomi Takahashi, both of Kobe, Japan

[73] Assignee: Kanegafuchi Kagaku Kogyo Kabushiki Kaisha, Osaka, Japan

[21] Appl. No.: 753,595

[22] Filed: Sep. 3, 1991

[30] Foreign Application Priority Data

Sep. 4, 1990 [JP] Japan ................................. 2-235445

[51] Int. Cl.$^5$ ............................................. C07D 333/78
[52] U.S. Cl. ............................................. 548/314
[58] Field of Search ........................................ 548/314

[56] References Cited

U.S. PATENT DOCUMENTS 4,230,869 10/1980 Yoneda et al. ...................... 548/314

Primary Examiner—Joseph Paul Brust
Assistant Examiner—M. S. H. Gabilan
Attorney, Agent, or Firm—Armstrong & Kubovcik

[57] ABSTRACT

A process for preparing a 5-arylhydantoin having the formula (II):

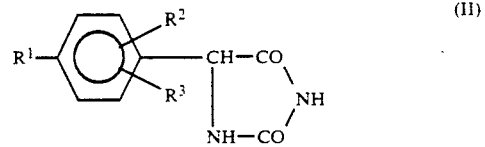

which comprises: reacting methyl 2-hydroxy-2-methoxyacetate, urea and an aryl compound having the formula (I):

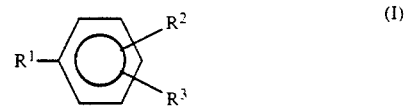

in the presence of an acid. According to the process, the 5-arylhydantoin which is a very effective intermediate for preparing D-arylglycines can be easily prepared from inexpensive raw materials in a high purity.

4 Claims, No Drawings

PROCESS FOR PREPARING 5-ARYLHYDANTOIN

BACKGROUND OF THE INVENTION

The present invention relates to a process for preparing 5-arylhydantoins. The 5-arylhydantoins are important compounds as a raw material for preparing D-2-arylglycines such as D-phenylglycine and D-p-hydroxyphenylglycine which are useful for preparing a semi-synthesized penicillin or cephalosporins.

The 5-arylhydantoins were, in the old days, prepared from a corresponding aryl aldehyde, ammonium carbonate and sodium cyanide according to Bucherer-Berg method, as discussed in Journal für Praktische Chemie, 1934, 140, 291. Also, various preparation methods of the 5-arylhydantoins have been known. For instance, Japanese Examined patent Publication No. 55-22474 discloses a method wherein glyoxylic acid, urea and phenol are reacted under an acidic condition. Japanese Examined patent Publication No. 55-16582 discloses a method wherein allantoin is reacted with phenol. Japanese Examined Patent Publication No. 57-57033 discloses a method wherein hydroxymandelic acid is reacted with urea. Japanese Unexamined Patent Publication No. 54-128572 discloses a method wherein glyoxylurea is reacted with phenol. Japanese Unexamined Patent Publication No. 54-138558 discloses a method wherein alloxanic acid is reacted with phenol. Japanese Unexamined patent Publication No. 54-138559 discloses a method wherein diglyoxylic acid triureide is reacted with phenol. Japanese Unexamined Patent Publication No. 54-138560 discloses a method wherein 5-hydroxyhydantoin is reacted with phenol.

According to Bucherer-Berg method, however, it is required to use sodium cyanide which is dangerous. Furthermore, the obtained crude hydantoin is contaminated with a large amount of a by-product or the obtained hydantoin is colored due to the oxidative side reaction of the phenol ring under an alkaline condition. Also, other methods as discussed above are unsatisfactory because the used raw materials, namely, glyoxylic acid, allantoin, hydroxymandelic acid, glyoxylurea, alloxanic acid, diglyoxylic acid triureide and 5-hydroxyhydantoin are expensive.

An object of the present invention is to provide a process for preparing 5-arylhydantoins from an unexpensive raw material, which has no defects as mentioned above.

This and the other objects of the present invention will become apparent from the following description hereinafter.

SUMMARY OF THE INVENTION

As a result of the earnest study in order to solve the above-mentioned defects, there has now been found out a process for preparing a 5-arylhydantoin from methyl 2-hydroxy-2-methoxyacetate which can be obtained from an unexpensive dialkyl maleate.

According to the present invention, there is provided a process for preparing a 5-arylhydantoin having the formula (II):

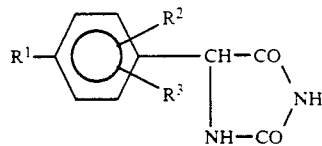

wherein $R^1$ is a hydroxyl group or a lower alkoxyl group, at least one position of the para-position and/or the ortho-positions with respect to the group $R^1$ is unsubstituted, each of $R^2$ and $R^3$ is independently a hydrogen atom, a hydroxyl group, a lower alkoxy group, a lower alkyl group, a halogen atom, an acylamino group or a nitro group which comprises: reacting methyl 2-hydroxy-2-methoxyacetate, urea and an aryl compound having the formula (I):

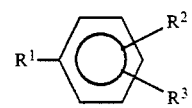

wherein $R^1$, $R^2$ and $R^3$ are as defined above in the presence of an acid.

DETAILED DESCRIPTION

It has been known that methyl 2-hydroxy-2-methoxyacetate (methyl hemi-acetal of methyl glyoxylate) which is the raw material used in the present invention can be prepared in a high yield from an unexpensive compound such as a dialkyl maleate by ozone oxidation, as discussed in Japanese Unexamined Patent Publication No. 59-21643. It is not necessary to use the purified methyl 2-hydroxy-2-methoxyacetate. Even the crude methyl 2-hydroxy-2-methoxyacetate obtained according to the above-mentioned preparation process can be used as it is.

The aryl compound used in the present invention is the aryl compound having the formula (I):

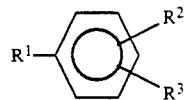

wherein $R^1$ is a hydroxyl group or a lower alkoxy group, preferably having 1 to 10 carbon atoms, at least one position of the para-position and/or the ortho-positions with respect to the group $R^1$ is unsubstituted, in other words, when the para-position or the ortho-position with respect to $R^1$ is substituted, the remaining ortho-position(s) and the para-position are unsubstituted, each of $R^2$ and $R^3$ is independently a hydrogen atom, a hydroxyl group, a lower alkoxy group, preferably having 1 to 10 carbon atoms, a lower alkyl group, preferably having 1 to 10 carbon atoms, a halogen atom, an acylamino group or a nitro group. A preferable aryl compound (I) is phenol.

As a reaction medium, an aqueous medium is preferably used. Water is the most practically used. Also, a mixture of water and an alcohol such as methanol or a mixture of water and acetic acid can be used as the reaction medium.

The reaction of the present invention can effectively proceed in the presence of the acid. As the acid, it is preferable to use a mineral acid such as hydrochloric acid or sulfuric acid. The concentration of the acid in the reaction system is from 0.5 to 12N. The yields of the 5-arylhydantoins tend to heighten with the increase of the acid concentration. However, the use of an excess of the acid might decompose the desired product. Accordingly, the preferably acid concentration is from 1 to 10N.

In the present invention, urea is used in an amount of at least 0.5 equivalent per molar equivalent of methyl 2-hydroxy-2-methoxyacetate. Since urea is decomposed in the acidic medium to form ammonia and $CO_2$, the amount of urea is preferably from 1.0 to 3.0 equivalents per molar equivalent of methyl 2-hydroxy-2-methoxyacetate. Also, the aryl compound (I) is used in an amount of at least 0.5 equivalent per molar equivalent of methyl 2-hydroxy-2-methoxyacetate. Since the use of an excess of the aryl compound (I) makes the purification difficult, the amount of the aryl compound (I) is preferably from 1.0 to 2.0 equivalents per molar equivalent of methyl 2-hydroxy-2-methoxyacetate.

The reaction is conducted at a temperature of, preferably not less than 30° C., more preferably from 60° to 95° C.

A necessary amount of methyl 2-hydroxy-2-methoxyacetate can be added previously at once to the solution containing urea and the aryl compound (I). Also, it can be added gradually added to the reaction system.

The prepared 5-arylhydantoins having the formula (II):

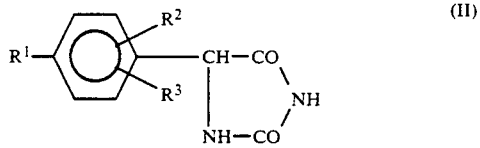

wherein $R^1$, $R^2$ and $R^3$ are as defined above can be very easily isolated from the reaction mixture. That is, since the desired products, the 5-arylhydantoins are, generally, slightly soluble in an acidic or neutral aqueous solution, during the reaction or after completing the reaction, the reaction mixture is cooled to easily precipitate it. Accordingly, the precipitate is separated from the reaction mixture (solid-liquid separation). It is possible that the obtained precipitate is subjected to a purification operation such as recrystallization to heighten the purity, as occasion demands.

The present invention is more specifically described and explained by means of the following Examples in which all percents are by weight unless otherwise noted. It is to be understood that the present invention is not limited to the Examples, and various changes and modifications may be made in the invention without departing from the spirit and scope thereof.

EXAMPLE 1

To a mixture of 28.2 g (0.30 mole) of phenol, 24.0 g (0.40 mole) of urea, 132 ml of water and 68 ml of concentrated hydrochloric acid was continuously added 48 g (0.20 mole) of a 50% aqueous solution of methyl 2-hydroxy-2-methoxyacetate at 70° C. for 10 hours with stirring. After completing the addition, the stirring was continued at 70° C. for 10 hours with heating. After completing the reaction, the reaction mixture was cooled to 50° C. to precipitate. After the precipitate was filtered off from the reaction mixture, it was washed with water then dried to give 23.5 g of 5-(4-hydoryphenyl)hydantoin. The purity was not less than 98% and the yield was 61.2%. The crystals had a melting point of 263° to 265° C. With respect to an infrared adsorption spectrum, NMR spectrum and Rf value of silica gel thin-layer chromatography, the crystals completely agreed with a sample prepared according to a known method as described in Japanese Examined Publication No. 22474/1980 (Rf=0.83, BuOH:CH$_3$CO$_2$H:H$_2$O=4:1:1).

EXAMPLE 2

A mixture of 2.82 g (0.03 mole) of phenol, 2.40 g (0.04 mole) of urea, 2.40 g (0.02 mole) of methyl 2-hydroxy-2-methoxyacetate, 9.8 ml of concentrated hydrochloric acid and 10.2 ml of water was reacted at 80° C. for 20 hours with stirring. The reaction mixture was diluted with a 50% aqueous solution of methanol. The yield of the produced 5-(4-hydoryphenyl)hydantoin was 1.86 g (46.5%) as determined by a high performance liquid chromatography.

Apparatus: Shimadzu LC-6A commercially available from Kabushiki Kaisha Shimadzu Seisakusho Column: YMC Packed Column A-303 S-5 120A ODS commercially available from Kabushiki Kaisha YMC Developing solvent: Phosphate buffer (pH 2.5) containing 10% of acetonitrile Flow rate: 1.3 ml/minute Detection: 210 nm, with UV Detector The retention time of 5-(4-hydroxyphenol)hydantoin was 4.0 minutes under such conditions.

According to the present invention, the 5-arylhydantoin can be easily obtained in a high purity by reacting methyl 2-hydroxy-2methoxyacetate, the aryl compound (I) such as phenol and urea in the presence of the acid with heating. That is, the present invention provides the preparation process of the remarkably effective intermediates for preparing D-arylglycines.

In addition to the ingredients used in the Examples, other ingredients can be used in the Examples as set forth in the specification to obtained substantially the same results.

What we claim is:

1. A process for preparing a 5-arylhydantoin having the formula (II):

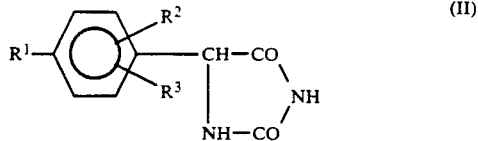

wherein $R^1$ is a hydroxyl group or a lower alkoxy group, at least one of the ortho-positions with respect to the group $R^1$ is unsubstituted, each of $R^2$ and $R^3$ is independently a hydrogen atom, a hydroxyl group, a lower alkoxy group, a lower alkyl group, a halogen atom, an acylamino group or a nitro group which comprises: reacting methyl 2-hydroxy-2-methoxyacetate, urea and an aryl compound having the formula (I):

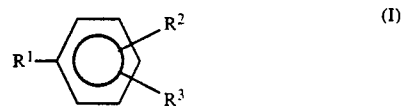

wherein R$^1$, R$^2$ and R$^3$ are as defined above in the presence of an acid.

2. The process of claim 1, wherein said aryl compound (I) is phenol.

3. The process of claim 1, wherein said acid is hydrochloric acid or sulfuric acid.

4. The process of claim 1, wherein said reaction is conducted in an aqueous medium.

* * * * *